United States Patent [19]

Kamochi et al.

[11] Patent Number: 5,455,256
[45] Date of Patent: Oct. 3, 1995

[54] SYNERGISTIC INSECTICIDAL COMPOSITIONS

[75] Inventors: Atumi Kamochi; Nobuhiro Yamashita, both of Kochi; Ikuya Saito; Yukio Kawahara, both of Kochi; Shin-ichi Tsuboi, Tochigi, all of Japan

[73] Assignee: Nihon Bayer Agrochem K.K., Tokyo, Japan

[21] Appl. No.: 209,940

[22] Filed: Mar. 11, 1994

[30] Foreign Application Priority Data

Mar. 18, 1993 [JP] Japan .................................. 5-082448

[51] Int. Cl.$^6$ .................................................. A01N 43/40
[52] U.S. Cl. ............................................................. 514/341
[58] Field of Search ................................................ 514/341

[56] References Cited

U.S. PATENT DOCUMENTS

| | | | |
|---|---|---|---|
| 4,725,589 | 2/1988 | Tsuboi et al. | 514/128 |
| 4,780,457 | 11/1988 | Tsuboi et al. | 514/89 |
| 4,914,113 | 4/1990 | Shiokawa et al. | 514/333 |
| 5,153,182 | 10/1992 | Tozzi | 514/67 |

FOREIGN PATENT DOCUMENTS 282706  1/1988  European Pat. Off. .

OTHER PUBLICATIONS

Australian Patent Abstract, No. AU-A-76565/87, pp. 753–754 (1987).
"Japanese Journal of Applied Enotomology and Zoology", vol. 35, 231–239 (1991) (Abstract).
Worthing et al, "The Pesticide Manual", 9th Ed. (1991) p. 491.

*Primary Examiner*—Allen J. Robinson
*Attorney, Agent, or Firm*—Sprung Horn Kramer & Woods

[57] ABSTRACT

An insecticidal composition comprising
(i) a compound of the formula

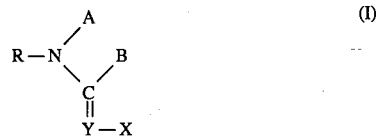 (I)

wherein
A is hydrogen, alkyl or a divalent group connected to B,
B is alkyl,

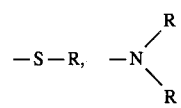

or a divalent group or atom connected to A,
R is hydrogen, acyl, alkyl or optionally substituted heteroarylalkyl,
Y is

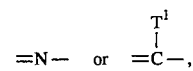

T$^1$ is hydrogen or optionally substituted alkyl, and
X is an electron attractive group, and
(ii) a synergistically effective amount of a methylenedioxybenzene derivative.

3 Claims, No Drawings

SYNERGISTIC INSECTICIDAL COMPOSITIONS

The present invention relates to novel insecticidal compositions.

Synergistically and cooperatively active insecticidal compositions were disclosed in British Patent No. 2,001,852 specification, Belgian Patent No. 861342 specification, French Patent No. 2,396,507 specification, U.S. Pat. No. 3,864,388 specification, U.S. Pat. No. 4,047,928 specification, U.S. Pat. No. 5,153,182 specification, Japanese Patent Application Disclosure No. Sho 58-126803 specification, and so on. Further, it has also been known to some extent that synergistic effects on insecticides can be obtained by using, as adjuvants, phosphates, carbamates, and pyrethroid series compounds.

It has become a pressing problem, in recent years, to control Thysanoptera represented by *Thrips palmi* Karny that seriously damages vegetables and flowering plants.

*Thrips palmi* Karny is known to devour plant tissues, thus hollowing the relevant cellular tissue, bleaching the leaves and eventually wilting and withering them when the damage is serious.

*Thrips palmi* Karny is known seriously to damage fruit-bearing plants and vegetables grown by house culture particularly in the Kyushu and Shikoku districts.

Further, Thysanoptera, compared to other pests, easily acquire resistance to commercially available pesticides (insecticides), posing a problem of finding a reliable control means to cope with the situation.

There have now been found novel insecticidal compositions comprising (i) compounds of the formula

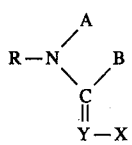

wherein

A is hydrogen, alkyl, or a divalent group connected to B,

B is alkyl,

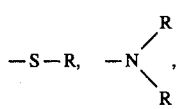

or a divalent group or atom connected to A,

R is hydrogen, acyl, alkyl or optionally substituted heteroarylalkyl,

Y is

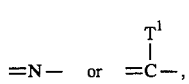

$T^1$ is hydrogen or optionally substituted alkyl, and

X is an electron attractive group, and (ii) a methylenedioxybenzene derivative.

Surprisingly, it has been found that the insecticidal compositions according to the present invention exhibit an insecticidal activity far higher than that shown by compounds of the general formula (I) and that such high activity is derived from the cooperative and synergistic effects of the combination of two kinds of active components.

In the compounds represented by the general formula (I), preferably,

A is hydrogen, $C_{1-6}$ alkyl, ethylene, trimethylene or

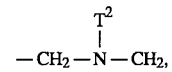

B is $C_{1-6}$ alkyl,

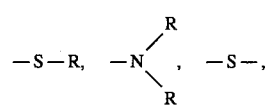

methylene or

wherein R and $T^2$ have the same meanings mentioned above,

R is hydrogen, formyl, $C_{1-4}$ alkylcarbonyl, benzoyl, $C_{1-4}$ alkylsulfonyl, $C_{1-6}$ alkyl or optionally substituted heteroarylmethyl having up to six ring atoms with at least one ring N atom, $T^2$ is hydrogen, $C_{1-4}$ alkyl or $C_{1-4}$ alkylcarbonyl, Y is =N- or =CH-, and X is nitro or cyano.

More preferably in the compounds represented by the general formula (I),

A is hydrogen, $C_{1-4}$ alkyl, ethylene, trimethylene or

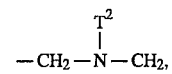

B is $C_{1-4}$ alkyl,

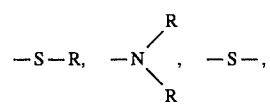

methylene or

R is hydrogen, formyl, acetyl, $C_{1-4}$ alkyl, 2-chloro-5-pyridylmethyl or 2-chloro-5-thiazolylmethyl, $T^2$ is methyl or ethyl, Y is =N- or =CH- , and X is nitro or cyano.

Especially preferred are those compounds represented by the general formula (I), wherein A is hydrogen, $C_{1-4}$ alkyl, ethylene, trimethylene, or

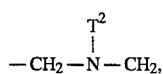

B is $C_{1-4}$ alkyl, -S-R,

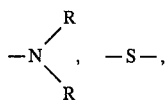

methylene or

wherein R and $T^2$ have the same meanings as mentioned above,

R is 2-chloro-5-pyridylmethyl or 2-chloro-5-thiazolylmethyl, $T^2$ is methyl or ethyl, Y is =N- or =CH-, and X is nitro or cyano.

Suitable examples of methylenedioxybenzene derivatives include 4-[1-[2(2-ethoxyethoxy)ethoxy]ethoxy]-1,2-methylenedioxybenzene (sesamex), 2-(1,3-benzodioxol-5-yl)-ethyl octyl sulfoxide (sulfoxide), 5-[bis[2-(2-butoxy-ethoxy)-ethoxy]methyl]-1,3-benzodioxole (piprotal), 1,3-benzodioxol-5-yl (1R,3aR,4S,6aR)-4-(1,3-benzodioxol-5-yl)perhydrofuro[3,4-c]furan-1-yl ether (sesasmolin), 4-(2,4-methylenedioxyphenyl)-5-methyl-m-dioxane (safroxan), 4-(3, 4-methylenedioxy-6-propylphenyl)-5-methyl-1,3-dioxane (safroxane), 1,4-di-(1,3-benzodioxol-5-yl)tetrahydrofuro[3,4-c]furan (sesamin) and especially piperonyl butoxide.

Examples of active compounds of the general formula (I) and employed in the insecticidal compositions according to the present invention are:

1- (6-chloro- 3-pyridylmethyl)-N-nitro-imidazolidin-2-ylideneamine,

N-cyano-N-(2-chloro-5-pyridylmethyl)-N'-methylacetoamidine,

1-[N-(6-chloro-3-pyridylmethyl)-N-ethylamino]-1-methylamino -2-nitrorethylene, 1-(2-chloro-5-pyridylmethyl)-5-methyl-2-nitroimino-hexahydro -1,3,5-triazine, 1-(2-chloro-5-thiazolylmethyl)-3,5-dimethyl-2-nitro-hexahydro -1,3,5-triazine, 1- (2-chloro-5-pyridylmethyl)-3,5-dimethyl-2-nitroimino-hexahydro -1,3,5-triazine, 1-(2-chloro-5-pyridylmethyl) -2-nitromethylene -imidazolidine, 1-[ N-(2-chloro-5-thiazolylmethyl)-N-ethylamino]-1-methylamino -2-nitroethylene, 3-(2-chloro-5-pyridylmethyl)-2-nitromethylene-thiazolidine, 1-(2-chloro-5-pyridylmethyl)-2-(1-nitro-2-allylthioethylidene) imidazolidine, 1-(2-chloro-5-pyridylmethyl)-2-(1-nitro-2-ethylthioethylidene) imidazolidine, 1-(2-chloro-5-pyridylmethyl)-2-(1-nitro-2-β-methylallylthio -ethylidene) imidazolidine, methyl-[3-(2-chloro-5-pyridylmethyl)-1-methyl-2-nitro] guanidino formate, 1-(2-chloro-5-pyridylmethylamino)-1-methylthio-2-nitroethylene, 1-(2-chloro-5-pyridylmethylamino)-1-methylamino-2-nitroethylene, 1-(2-chloro-5-pyridylmethyl)-3-nitro-2-methylisothiourea, 3-(2-chloro-5-pyridylmethyl)-1-methyl-2-nitroguanidine, 1-(2-chloro-5-pyridylmethylamino) -1-dimethylamino-2-nitroethylene, 1-[N-(2-chloro-5-pyridylmethyl)-N-methylamino]-1-methylamino -2-nitroethylene, 1--[N-(2-chloro-5-pyridylmethyl)-N-methylamino]-1-dimethylamino -2-nitroethylene, 3-(2-chloro-5-pyridylmethyl)-1,1-dimethyl-2-nitroguanidine, 1-(2-chloro-5-pyridylmethylamino)-1-ethylamino-2-nitroethylene, 1-amino-1-[N-(2-chloro-5-pyridylmethyl)-N-methylamino]-2-nitroethylene, 3-(2-chloro-5-pyridylmethyl)-1,3-dimethyl-2-nitroguanidine, 3-(2-chloro-5 -pyridylmethyl)-1,1,3-trimethyl -2-nitroguanidine, 1-amino-1-[N-(2-chloro-5-pyridylmethyl)-N-ethylamino] -2-nitroethylene, 1-[N-(2-chloro-5-pyridylmethyl)-N -n-propylamino] -1-methylamino -2-nitroethylene, 1-[N-(2-chloro-5-pyridylmethyl)-N -ethylamino]-1-ethylamino -2-nitroethylene, and 3-(2-chloro-5-pyridylmethyl)-3-ethyl-1-methyl-2 -nitroguanidine, etc.

The compounds recited hereinabove are merely illustrative.

The weight ratios of the active compounds of the instant insecticidal compositions may be varied within a wide range.

In general, per part by weight of the compound of general formula (I), there may be present about 1 to 50 parts by weight, preferably about 1 to 25 parts by weight, of the methylenedioxy benzene derivative.

The insecticidally active compositions according to the present invention exhibit excellent insecticidal activities, wherefore they are advantageously employed as insecticidal agents in such uses as foliar application, underwater or submerged application, solid treatment, soil incorporation application, seedling box treatment, stalk injection and planting treatment, etc.

Furthermore, the insecticidal compositions according to the present invention have a very low level of phytotoxicity to plants under cultivation and toxicity to warm-blooded animals, so that the present compositions can be effectively used for controlling various pests and hygienic insects, particularly insect pests, to ensure protection of agricultural products, forestry products, stored crop products, and artifacts. These compositions are usually very active on both susceptible and resistant seeds for a prolonged period of time or for a certain stage of growth.

Particularly, the insecticidal compositions according to the present invention can be employed for effectivity controlling Thysanoptera, planthoppers belonging to the order of Hemiptera, especially brown planthopper (*Nilaparvata lugens*), white-backed planthopper (*Sogatella furcifera*), smaller brown planthopper (*Laodelphax striatellus*), leafhoppers, aphis and the like, paddy field insect pests and various insect pests inhabiting various horticultural crops such as fruit trees and vegetables.

In addition to the above-mentioned pest control, the insecticidal compositions according to the present invention exhibit a very remarkable insecticidal activity against a wide field of insect pests as set forth hereinbelow due to cooperative and synergistic effects. Representative insects include the following:

From the order of Coleoptera, e.g. *Callosobruchus chinensis, Sitophilus zeamais, Tribolium castancum, Epilachna vigintioctomaculata, Agriotes fuscicollis, Anomala rufocuprea, Leptinotarsa decemlineata,* Diabrotica supp., *Monochamus alternatus, Lissorhoptrus oryzophilus, Lyctus bruneus;* from the order of Lepidoptera, e.g., *Lymantria dispar, Malacosoma neustria, Pieris rapae, Spodoptera litura, Mamestra brassicae, Chilo suppressalis, Pyrausta nubilalis, Ephestia cautella, Adoxophyes orana, Carpocapsa pomonella, Agrotis fucosa, Galleria mellonella, Plutella maculipennis, Heliothis virescens, Phyllocnistis citrella;* from the order of Hemiptera, e.g. *Nephotettix cincticeps, Nilaparvata lugens, Pseudococcus comstocki, Unaspis yanonensis, Myzus persicae, Aphis pomi, Aphis gossypii, Rhopalosiphum pseudobrassicas, Stephanitis nashi,* Nezara spp., *Cimex lectularius, Trialeurodes vaporariorum,* Psylla spp.; from the order of Orthoptera, e.g. *Blatella germanica, Periplaneta americana, Gryllotalpa africana, Locusta migratoria migratoriodes;* from the order of Isoptera, e.g. *Deucotermes speratus, Coptotermes formosanus;* from the order of Thysanoptera, e.g. *Thrips palmi* Karny; from the order of Diptera, e.g. *Musca domestica, Aedes aegypti, Hylemia platura; Celux pipiens, Anopheles slnensis, Culex tritaeniorhynchus.*

The insecticidal compositions according to the present invention can be formulated into either mixtures of active compound partners per se or as conventional formulations, such as solutions, emulsions, suspensions, wettable powders, powders, foams, pastes, granules, tablets, solid agents, aerosols, natural and synthetic materials impregnated with active compounds, microcapsules, coating compositions for use on seeds, and formulations used with burning equipment, such as fumigating cartridges, fumigating cans and fumigating coils, as well as ULV cold mist and warm mist formulations.

These formulations may be produced in known manner, for example, by mixing the active compounds with extenders, that is to say liquid or liquefied gaseous or solid diluents or carriers, optionally with the use of surface active agents, that is to say emulsifying agents, dispersing agents, and/or foam-forming agents. In the case of using water as an extender, organic solvents can, for example, also be used as auxiliary solvents.

As liquid diluents or carriers may be mentioned, in general, aromatic hydrocarbons, such as xylene, toluene and alkyl naphthalenes, chlorinated aromatic or chlorinated aliphatic hydrocarbons, such as chlorobenzenes, chloroethylenes and methylene chloride, aliphatic or alicyclic hydrocarbons, such as cyclohexane or paraffins, for example, mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimethylsulfoxide, as well as water.

By liquefied gaseous diluents or carriers are meant liquids which are gaseous at normal temperature and under normal pressure, for example, aerosol propellants, such as halogenated hydrocarbons as well as butane, propane, nitrogen and carbon dioxide.

As solid diluents there may be used ground natural minerals, such as kaolins, clays, talc, chalk, quartz, attapulgite, montmorillonite or diatomaceous earth, and ground synthetic minerals, such as highly-dispersed silicic acid, alumina and silicates.

As solid carriers for granules there may be used crushed and fractionated natural rocks such as calcite, marble, pumice, sepiolite and dolomite, as well as synthetic granules of inorganic and organic meals, and granules of organic materials such as sawdust, coconut shells, corn cobs and tobacco stalks.

As emulsifying and/or foam-forming agents there may be used non-ionic and anionic emulsifiers, such as polyoxyethylene-fatty acid esters, polyoxyethylene-fatty alcohol ethers, for example, alkylaryl polyglycol ethers, alkylsulfonates, alkylsulfates, arylsulfonates as well as albumin hydrolysis products. Dispersing agents include, for example, lignin sulfite waste liquors and methyl cellulose.

Adhesives such as carboxymethyl cellulose and natural and synthetic polymers, (such as gum arabic, polyvinyl alcohol and polyvinyl acetate) can be used in the Formulations in the form of powders, granules or emulsifiable concentrations.

It is possible to use colorants such as inorganic pigments, for example, iron oxide, titanium oxide and Prussian Blue, and organic dyestuffs, such as alizarin dyestuffs, azo dyestuffs or metal phthalocyanine dyestuffs, and trace elements, such as salts of iron, manganese, boron, copper, cobalt, molybdenum and zinc.

The formulations, contain for example, from 0.1 to 95 percent by weight of active compounds, preferably from 0.5 to 90 percent by weight.

The insecticidal compositions of the present invention can be used as such, as their commercially useful formulations or as the use forms prepared therefrom, optionally together with other active agents such as for example, insecticides, poisonous baits, bactericides, acaricides, nematicides, fungicides, growth regulators or herbicides. Examples of the pesticides include, e.g., those derived from organic phosphates, carbamates, carboxylates, chlorohydrocarbons, carboxylates and antibiotic products.

The content of the insecticidal compositions of the present invention in the formulations of the types that are commercially available can vary within a substantially wide range, that is, from about 0.00001 to 100 percent by weight, preferably from 0.001 to 1 percent by weight.

The insecticidal compositions according to the present invention may be used in conventional manner adapted to the particular formulations.

When used against pests harmful to health and to stored products, the active compounds are distinguished by an excellent residual activity on wood and soil as well as a good stability to alkali on limed substrates.

The present invention will be further described in the following illustrative examples wherein all parts are by weight unless otherwise expressed.

EXAMPLE

Test Example 1

Insecticidal test on *Thrips palmi* Karny

Compounds under test

No. 1: 1-(6-chloro-3-pyridylmethyl)-N-nitro-imidazolidin -2-ylideneamine,

No. 2: N-cyano-N-(6-chloro-3-pyridylmethyl)-N'-methylacetoamidine,

No. 3: 1-[N-(6-chloro-3-pyridylmethyl)-N-ethylamino]-1-methylamino -2-nitroethylene, No. 4: 1-(2-chloro-5-thiazolylmethyl)-3,5-dimethyl-2-nitroimino-hexahydro-1,3,5-triazine, PB : Piperonyl butoxide Preparation of test formulation:

solvent: 3 parts by weight of xylene

Emulsifier: 1 part by weight of polyoxyethylene-alkylphenyl-ether

To prepare suitable formulations of active compounds, 1part by weight of each of the active compounds was mixed with the above-mentioned amount of the emulsifier, and the mixture was diluted with water to the predetermined concentration.

Test Method:

The present method was aimed at preventing the flight and propagation of *Thrips palmi* Karny from one place to another.

As the test plants there were used eggplants (Senryo No. 2 variety). Into unglazed pottery basins each having a diameter of about 15 cm there were transplanted seedlings of eggplants with from four to five open leaves and, one week before spraying thereon the insecticidal compositions, the plants were inoculated with adult insects. Thus, at the time of spraying of the insecticidal compositions there were already present *Thrips palmi* Karny in all the growth stages from eggs to adults, not only in and on the plants but also in the soil. In the test, one area consisted of three basins. Immediately before spraying, the total number of insects were counted and classified as adults or larvae. The spraying of the insecticidal compositions was carried out with use of a spraying gun such that 100 ml of each of the insecticidal compositions was applied to three seedlings until the leaf surfaces thereof were moistened sufficiently with each of the formulations at varying concentrations that had been prepared according to the procedures stated hereinbefore. Immediately after spraying, each of the basins was covered with a cylindrical glass having a diameter of 15 cm and a height of 35 cm with its lower portion being secured into the basin by an adhesive vinyl tape and with its upper portion covered with a cotton cloth secured thereto with a rubber band, and it was thereafter kept at 20° C. After two days and seven days, respectively, a survey was carried out to count the total number of the insects, classified as adult insects or larvae, obtaining a protective index calculated according to the following equation:

$$\text{Protective index} = \left[ 1 - \left( \frac{A}{B} \div \frac{C}{D} \right) \right] \times 100$$

wherein

A is the number of insects in the treated zone after spraying the insecticidal composition B is the number of insects in the treated zone before spraying of the insecticidal composition, C is the number of insects in the untreated zone after spraying of the insecticidal composition, D is the number of insects in the untreated zone before spraying of the insecticidal composition.

The results are shown in Table 1.

TABLE 1

| Compounds under test | Concentrations of active components ppm | Protective index after two days adult | Protective index after two days larvae | Protective index after seven days adult | Protective index after seven days larvae |
|---|---|---|---|---|---|
| No. 1 + PB | 50 + 450 | 100 | 100 | 100 | 100 |
|  | 25 + 225 | 100 | 100 | 100 | 100 |
| No. 1 | 50 | 100 | 100 | 98 | 100 |
|  | 25 | 70 | 75 | 60 | 70 |
| PB | 450 | 0 | 0 | 0 | 0 |
| Untreated | — | 0 | 0 | 0 | 0 |

In addition, compounds Nos. 2, 3 and 4 exhibited similar synergistic effects with piperonyl butoxide.

It will be understood that the specification and examples are illustrative but not limitative of the present invention and that other embodiments within the spirit and scope of the invention will suggest themselves to those skilled in the art.

We claim:

1. An insecticidal composition comprising 1-(6-chloro-3-pyridyl-methyl)-N-nitro-imidazolidin-2-ylideneamine and a synergistically effective amount of piperonyl butoxide in a weight ratio ranging from about 1:1 to 1:50.

2. A composition according to claim 1, wherein the weight ratio ranges from about 1:1 to 1:25.

3. A method of combating insects which comprises applying to such insects or to an insect habitat an insecticidally effective amount of a composition according to claim 1.

* * * * *